US011116566B2

(12) United States Patent
Dinger et al.

(10) Patent No.: US 11,116,566 B2
(45) Date of Patent: Sep. 14, 2021

(54) SOFT PALATE TREATMENT

(71) Applicant: AERIN MEDICAL, INC., Sunnyvale, CA (US)

(72) Inventors: Fred Dinger, Sunnyvale, CA (US); Andrew Frazier, Sunnyvale, CA (US); Scott J. Wolf, Menlo Park, CA (US)

(73) Assignee: Aerin Medical, Inc., Sunnyvale, CA (US)

( * ) Notice: Subject to any disclaimer, the term of this patent is extended or adjusted under 35 U.S.C. 154(b) by 417 days.

(21) Appl. No.: 15/848,951

(22) Filed: Dec. 20, 2017

(65) Prior Publication Data
US 2018/0177546 A1  Jun. 28, 2018

Related U.S. Application Data

(60) Provisional application No. 62/438,300, filed on Dec. 22, 2016.

(51) Int. Cl.
*A61B 18/14* (2006.01)
*A61F 5/56* (2006.01)
(Continued)

(52) U.S. Cl.
CPC .......... *A61B 18/1477* (2013.01); *A61B 18/04* (2013.01); *A61B 18/1485* (2013.01);
(Continued)

(58) Field of Classification Search
CPC ... A61F 5/56; A61N 2005/0606; A61N 5/045; A61N 1/06; A61N 1/0548; A61N 1/403; A61N 2007/0043; A61B 18/1477; A61B 18/04; A61B 18/1485; A61B 18/1815; A61B 2018/00702; A61B 18/1442; A61B 18/02; A61B 2018/00761; A61B 2018/00642; A61B 2018/0016;
(Continued)

(56) References Cited

U.S. PATENT DOCUMENTS 4,887,605 A   12/1989  Angelsen et al.
5,348,008 A    9/1994  Bomn et al.
(Continued)

FOREIGN PATENT DOCUMENTS

CN       2621723 Y      6/2004
CN     101325919       12/2008
(Continued)

OTHER PUBLICATIONS

International Search Report and Written Opinion for PCT/US2017/067596, dated Mar. 14, 2018, 15 pages.
(Continued)

*Primary Examiner* — Thomas A Giuliani
(74) *Attorney, Agent, or Firm* — Merchant & Gould P.C.

(57) ABSTRACT

A method of treating a soft palate in a patient to treat sleep apnea, snoring or both may involve advancing a treatment element of a treatment device through the patient's mouth, contacting a tissue-contact surface of the treatment element with the soft palate, delivering energy to the soft palate via one or more energy delivery members on the tissue-contact surface, and removing the treatment element from the mouth.

8 Claims, 8 Drawing Sheets

(51) Int. Cl.

| | | |
|---|---|---|
| *A61B 18/18* | (2006.01) | |
| *A61N 1/40* | (2006.01) | |
| *A61B 18/04* | (2006.01) | |
| *A61N 1/06* | (2006.01) | |
| *A61N 1/05* | (2006.01) | |
| A61N 5/06 | (2006.01) | |
| A61N 5/04 | (2006.01) | |
| A61B 18/00 | (2006.01) | |
| A61B 18/02 | (2006.01) | |
| A61N 7/00 | (2006.01) | |

(52) U.S. Cl.
CPC ............ *A61B 18/1815* (2013.01); *A61F 5/56* (2013.01); *A61N 1/0548* (2013.01); *A61N 1/06* (2013.01); *A61N 1/403* (2013.01); *A61B 18/02* (2013.01); *A61B 18/1442* (2013.01); *A61B 2018/0016* (2013.01); *A61B 2018/00327* (2013.01); *A61B 2018/00642* (2013.01); *A61B 2018/00702* (2013.01); *A61B 2018/00761* (2013.01); *A61B 2018/00821* (2013.01); *A61B 2018/143* (2013.01); *A61B 2018/1467* (2013.01); *A61N 5/045* (2013.01); *A61N 2005/0606* (2013.01); *A61N 2007/0043* (2013.01)

(58) Field of Classification Search
CPC .... A61B 2018/00327; A61B 2018/143; A61B 2018/00821; A61B 2018/1467; A61B 2018/00214; A61B 2018/00273; A61B 2018/00791; A61B 2018/126
USPC .... 606/41, 42, 48–50; 607/98, 99, 101, 102, 607/113, 115, 116
See application file for complete search history.

(56) References Cited

U.S. PATENT DOCUMENTS

| | | |
|---|---|---|
| 5,533,499 A | 7/1996 | Johnson |
| 5,542,916 A | 8/1996 | Hirsch et al. |
| 5,624,439 A | 4/1997 | Edwards et al. |
| 5,674,191 A | 10/1997 | Edwards et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A * | 12/1998 | Edwards ................ A61N 5/045 604/22 |
| 5,843,077 A | 12/1998 | Edwards |
| 5,846,235 A | 12/1998 | Pasricha et al. |
| 5,879,349 A | 3/1999 | Edwards |
| 5,938,659 A | 8/1999 | Tu |
| 6,026,816 A | 2/2000 | McMillan et al. |
| 6,045,549 A | 4/2000 | Smethers et al. |
| 6,096,033 A | 8/2000 | Tu et al. |
| 6,102,907 A | 8/2000 | Smethers et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,293,941 B1 | 9/2001 | Strul et al. |
| 6,309,386 B1 | 10/2001 | Bek |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,416,491 B1 | 7/2002 | Edwards et al. |
| 6,425,151 B2 | 7/2002 | Bamett |
| 6,431,174 B1 | 8/2002 | Knudson et al. |
| 6,451,013 B1 | 9/2002 | Bays et al. |
| 6,502,574 B2 | 1/2003 | Stevens |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,659,106 B1 | 12/2003 | Hovda et al. |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,416,550 B2 | 8/2008 | Protsenko et al. |
| 7,442,191 B2 | 10/2008 | Hovda et al. |
| 7,678,069 B1 | 3/2010 | Baker et al. |
| 7,780,730 B2 | 8/2010 | Saidi |
| 7,824,394 B2 | 11/2010 | Manstein |
| 7,850,683 B2 | 12/2010 | Elkins et al. |
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| D716,325 S | 10/2014 | Brudnicki |
| 8,925,551 B2 | 1/2015 | Sanders |
| 8,936,594 B2 | 1/2015 | Wolf et al. |
| 8,986,301 B2 | 3/2015 | Wolf et al. |
| 9,072,597 B2 | 7/2015 | Wolf et al. |
| 9,119,954 B2 | 9/2015 | Burdette et al. |
| 9,125,677 B2 | 9/2015 | Sobol |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,452,087 B2 | 1/2016 | Holm et al. |
| D763,910 S | 8/2016 | Drozd et al. |
| D765,091 S | 8/2016 | Del Lima et al. |
| 9,415,194 B2 | 8/2016 | Wolf et al. |
| D765,718 S | 9/2016 | Vinna et al. |
| 9,433,463 B2 | 9/2016 | Wolf et al. |
| 9,452,010 B2 | 9/2016 | Wolf et al. |
| 9,486,278 B2 | 11/2016 | Wolf et al. |
| 9,526,571 B2 | 12/2016 | Wolf et al. |
| 9,526,652 B2 | 12/2016 | Harrison et al. |
| D776,717 S | 1/2017 | Asai |
| D789,383 S | 6/2017 | Bawazeer et al. |
| 9,687,288 B2 | 6/2017 | Saadat |
| 9,687,296 B2 | 6/2017 | Wolf et al. |
| D795,898 S | 8/2017 | Li et al. |
| D797,756 S | 9/2017 | Meyer et al. |
| 9,763,723 B2 | 9/2017 | Saadat |
| 9,763,743 B2 | 9/2017 | Lin |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,780 B2 | 7/2018 | Wolf et al. |
| 10,028,781 B2 | 7/2018 | Saadat |
| D840,428 S | 2/2019 | Narinedhat et al. |
| D844,013 S | 3/2019 | Peeters et al. |
| D857,034 S | 8/2019 | Hung et al. |
| D874,492 S | 2/2020 | Henderson |
| D875,742 S | 2/2020 | Kang et al. |
| D877,171 S | 3/2020 | Poindexter et al. |
| D881,904 S | 4/2020 | Angeles et al. |
| D902,412 S | 11/2020 | Angeles et al. |

(56) References Cited

U.S. PATENT DOCUMENTS

| | | | |
|---|---|---|---|
| 2002/0016588 A1 | 2/2002 | Wong et al. | |
| 2002/0049464 A1 | 4/2002 | Donofrio et al. | |
| 2002/0087155 A1 | 7/2002 | Underwood et al. | |
| 2002/0128641 A1 | 9/2002 | Underwood et al. | |
| 2003/0139789 A1* | 7/2003 | Tvinnereim | A61B 18/1485 607/99 |
| 2003/0144659 A1 | 7/2003 | Edwards | |
| 2003/0208194 A1 | 11/2003 | Hovda et al. | |
| 2003/0225403 A1 | 12/2003 | Woloszko et al. | |
| 2004/0220644 A1 | 11/2004 | Shalev et al. | |
| 2005/0020901 A1 | 1/2005 | Belson | |
| 2005/0119643 A1 | 6/2005 | Sobol et al. | |
| 2005/0222565 A1 | 10/2005 | Manstein | |
| 2005/0234439 A1* | 10/2005 | Underwood | A61B 18/1485 606/32 |
| 2005/0240147 A1 | 10/2005 | Makower et al. | |
| 2005/0288655 A1 | 12/2005 | Root et al. | |
| 2005/0288665 A1 | 12/2005 | Woloszko et al. | |
| 2006/0235377 A1 | 10/2006 | Earley | |
| 2006/0253117 A1 | 11/2006 | Hovda et al. | |
| 2006/0276817 A1 | 12/2006 | Vassallo et al. | |
| 2006/0276861 A1 | 12/2006 | Lin | |
| 2007/0066944 A1 | 3/2007 | Nyte | |
| 2007/0073282 A1 | 3/2007 | McGarrigan et al. | |
| 2007/0219600 A1 | 9/2007 | Gertner et al. | |
| 2008/0027423 A1 | 1/2008 | Choi et al. | |
| 2008/0027480 A1 | 1/2008 | van der Burg et al. | |
| 2008/0082090 A1 | 4/2008 | Manstein | |
| 2008/0125626 A1 | 5/2008 | Chang et al. | |
| 2008/0312644 A1 | 12/2008 | Fourkas | |
| 2009/0018485 A1 | 1/2009 | Krespi et al. | |
| 2009/0124958 A1 | 5/2009 | Li | |
| 2009/0143821 A1 | 6/2009 | Stupak | |
| 2009/0292358 A1 | 11/2009 | Saidi | |
| 2010/0144996 A1 | 6/2010 | Kennedy et al. | |
| 2010/0152730 A1 | 6/2010 | Makower et al. | |
| 2010/0174283 A1 | 7/2010 | McNall | |
| 2010/0241112 A1 | 9/2010 | Watson | |
| 2011/0009737 A1 | 1/2011 | Manstein | |
| 2011/0282268 A1 | 11/2011 | Baker et al. | |
| 2012/0039954 A1 | 2/2012 | Cupit et al. | |
| 2012/0078377 A1 | 3/2012 | Gonzales et al. | |
| 2012/0298105 A1 | 11/2012 | Osorio | |
| 2012/0316473 A1 | 12/2012 | Bonutti et al. | |
| 2012/0316557 A1 | 12/2012 | Sartor et al. | |
| 2012/0323227 A1 | 12/2012 | Wolf et al. | |
| 2012/0323232 A1 | 12/2012 | Wolf et al. | |
| 2013/0218158 A1 | 8/2013 | Danek et al. | |
| 2014/0088463 A1* | 3/2014 | Wolf | A61B 18/1442 601/2 |
| 2014/0114233 A1 | 4/2014 | Deem et al. | |
| 2015/0202003 A1 | 7/2015 | Wolf et al. | |
| 2016/0058336 A1 | 3/2016 | Blahnik et al. | |
| 2016/0317803 A1* | 11/2016 | Sama | A61N 1/0548 |
| 2017/0095288 A1 | 4/2017 | Wolf et al. | |
| 2017/0209199 A1 | 7/2017 | Wolf et al. | |
| 2017/0224987 A1 | 8/2017 | Kent et al. | |
| 2017/0231651 A1 | 8/2017 | Dinger et al. | |
| 2017/0245924 A1 | 8/2017 | Wolf et al. | |
| 2017/0252089 A1 | 9/2017 | Hester | |
| 2017/0252100 A1 | 9/2017 | Wolf et al. | |
| 2017/0357419 A1 | 12/2017 | Raymann et al. | |
| 2017/0360495 A1 | 12/2017 | Wolf et al. | |
| 2018/0000535 A1 | 1/2018 | Wolf et al. | |
| 2018/0177542 A1 | 6/2018 | Wolf et al. | |
| 2018/0185085 A1 | 7/2018 | Wolf et al. | |
| 2018/0228533 A1 | 8/2018 | Wolf et al. | |
| 2018/0263678 A1 | 9/2018 | Saadat | |
| 2018/0317997 A1 | 11/2018 | Dinger et al. | |
| 2020/0129223 A1 | 4/2020 | Angeles et al. | |
| 2020/0268439 A1 | 8/2020 | Frazier et al. | |

FOREIGN PATENT DOCUMENTS

| | | |
|---|---|---|
| CN | 101883606 A | 11/2010 |
| CN | 103055417 A | 4/2013 |
| DE | 102007006467 B3 | 3/2008 |
| WO | 199907299 | 2/1999 |
| WO | 2001043653 | 6/2001 |
| WO | 2003024349 | 3/2003 |
| WO | 2007037895 | 4/2007 |
| WO | 2007134005 | 11/2007 |
| WO | WO2009048580 A1 | 4/2009 |
| WO | 2010077980 | 7/2010 |
| WO | 2012174161 | 12/2012 |
| WO | 2015047863 | 4/2015 |
| WO | 2015048806 | 4/2015 |
| WO | 2015153696 | 10/2015 |

OTHER PUBLICATIONS

Nesmiyanov, Nikita. "12 Open Source/Commercial Control Panels for Virtual Machines (VM's) Management." TecMint, published Jul. 28, 2016 (Retrieved from the Internet Feb. 19, 2020). Internet URL: <https://www.tecmint.com/opensource-commercial-control-panels-manage-virtual-machines/> (Year: 2016).

"Electrosurgery Console", U.S. Appl. No. 29/668,608, filed Oct. 31, 2018, 12 pages.

"Non-Invasive Nasal Airway Remodeling." Aerin Medical, published Sep. 27, 2017 (Retrieved from the Internet Jan. 30, 2020).

Darville, Fabien. "Progress Bar." Behance, published May 3, 2013 (Retrieved from the Internet Jan. 30, 2020). Internet URL: <https://www.behance.net/gallery18490779/Progress-bar> (Year: 2013).

* cited by examiner

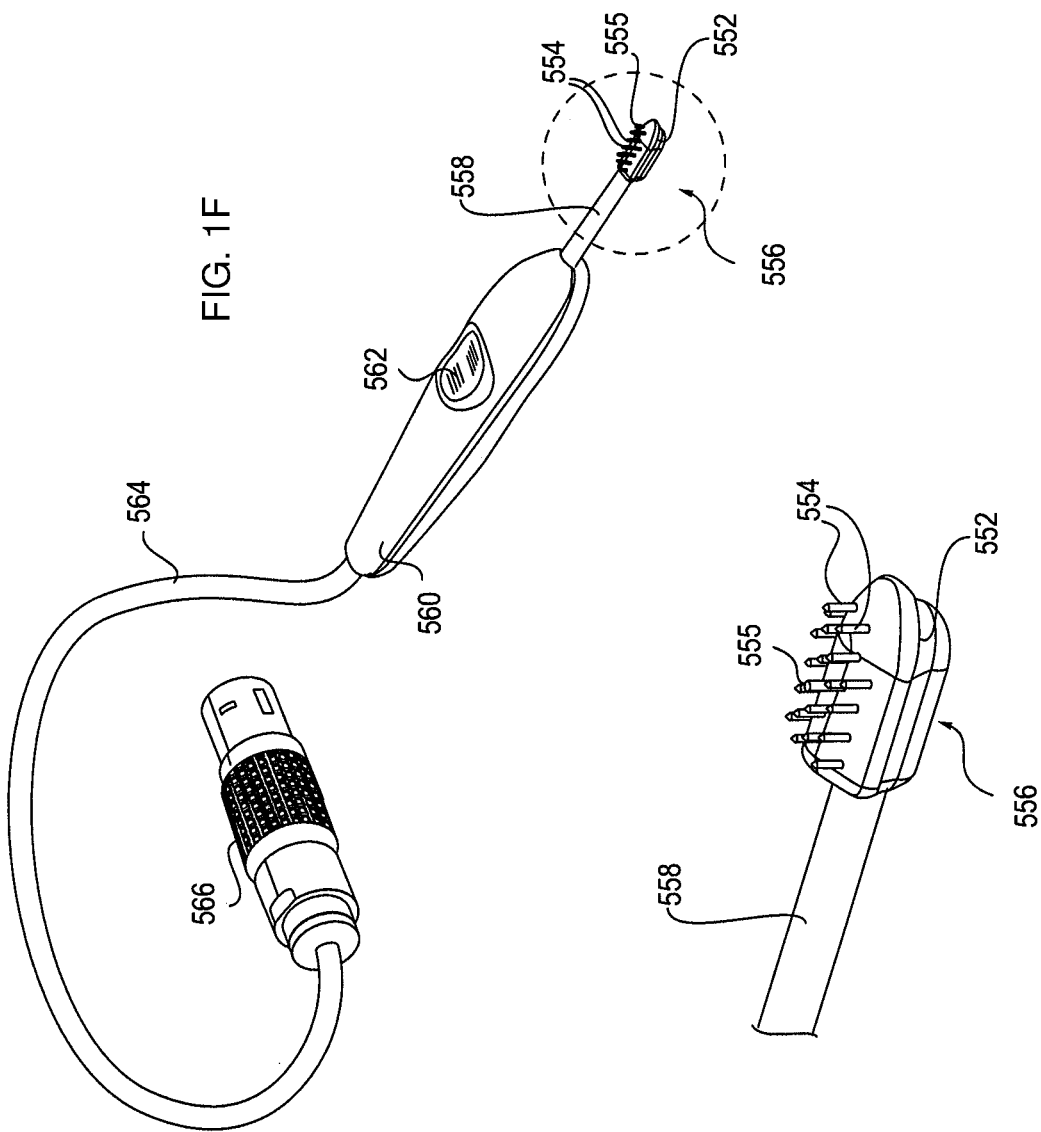

SOFT PALATE TREATMENT

CROSS-REFERENCE TO RELATED APPLICATIONS

This application claims priority to U.S. Provisional Patent Application Ser. No. 62/438,300, titled "Soft Palate Treatment," filed Dec. 22, 2016. The aforementioned provisional patent application is hereby incorporated fully by reference.

TECHNICAL FIELD

This application relates generally to the field of medical devices and treatments. In particular, the application relates to systems, devices and methods for treating the soft palate and possibly other parts of the mouth, to improve breathing and specifically to treat snoring and/or sleep apnea.

BACKGROUND

Snoring and sleep apnea are extremely prevalent and significant health issues in the United States and other parts of the world. Sleep apnea is defined as the cessation of breathing during sleep. Obstructive sleep apnea (OSA) is the most common form of sleep apnea, and it is often linked to obesity, which is becoming an ever more prevalent health condition. OSA occurs when the tissues in the back of the throat repetitively collapse during sleep, producing snoring and complete airway blockage. This blockage creates pauses in breathing that occur repeatedly every night. In severe cases, they can occur as frequently as every 30 seconds. Alarmingly, they can last up to a full minute.

The repetitive pauses in breathing during sleep in an OSA sufferer are accompanied by a reduction in blood oxygen levels and are followed by an arousal response. This response includes a release of substances into the bloodstream, which promote elevation of blood pressure, inflammation, insulin resistance, and a disruption of the brain wave sleep pattern. The consequences of untreated sleep apnea include poor quality sleep, excessive daytime fatigue and sleepiness, irritability, hard-to-control high blood pressure and diabetes, heart disease and stroke. Moreover, untreated sleep apnea may be responsible for job impairment and motor vehicle crashes.

Snoring, which is typically a less serious and severe condition than sleep apnea, still has significant effects on people who suffer from it and their loved ones. Snoring can affect a person's sleep and of course can also disrupt the sleep of a spouse, sibling or others who are sleeping nearby.

Many different methods and devices have been developed and tested for treating sleep apnea and snoring, but no perfect solution has yet been discovered. Some treatments for sleep apnea involve major, invasive surgery, for example to remove portions of the tongue and/or throat or to place mechanical slings or other implants in the tongue, in an effort to prevent the tongue from falling back in the mouth during sleep. Less invasive techniques, such as wearing an adhesive nasal strip to bed each night, are usually less effective or do not work at all, since many OSA patients are either already mouth breathers or convert to mouth breathing when a nasal blockage is addressed.

Therefore, it would be highly advantageous to have improved systems, devices and methods for treating sleep apnea and snoring. Ideally, these improved systems and techniques would be relatively less invasive than most of the surgical techniques used currently or tried in the past, while still working effectively for many patients. It would also be ideal if these techniques did not involve implants. The present disclosure will address at least some of these objectives.

BRIEF SUMMARY

Embodiments of the present application are directed to devices, systems and methods for treating the soft palate and possibly other areas of the mouth and/or throat, to treat sleep apnea and/or snoring. Various embodiments may be used to reshape, remodel, strengthen, stiffen or change properties of tissues of the soft palate, including but not limited to skin, muscle, mucosa, submucosa and/or cartilage of the soft palate. This change in the soft palate may prevent collapse of the soft palate or vibration of the soft palate during nighttime breathing and thus prevent or at least reduce OSA and/or snoring.

According to one aspect of the present disclosure, a method of treating a soft palate in a patient to treat sleep apnea, snoring or both may involve advancing a treatment element of a treatment device through the patient's mouth, contacting a tissue-contact surface of the treatment element with the soft palate, delivering energy to the soft palate via one or more energy delivery members on the tissue-contact surface, and removing the treatment element from the mouth. In some embodiments, the energy delivery members are two rows of bipolar, radiofrequency electrode pairs protruding from the tissue-contact surface, and delivering the energy involves delivering radiofrequency energy between the two rows of electrode pairs, to reshape, remodel, strengthen and/or change a property of the soft palate.

In some embodiments, the method may also involve applying force against the soft palate with the tissue-contact surface to at least temporarily deform tissue of the soft palate. Some embodiments may also involve forming an incision in mucosal tissue of the soft palate, in which case the energy may be delivered to submucosal tissue. The type of delivered energy may be radiofrequency (monopolar or bipolar), microwave, ultrasound, heat, cryogenic energy (energy removal) or the like. The method may also involve repositioning the treatment element to a new location on the soft palate and repeating the delivering step, before removing the treatment element from the mouth. This may be repeated as many times as desired, to cover a given area of the soft palate.

Optionally, some embodiments may also include injecting a substance into the soft palate before applying energy to the tissue. For example the substance may be an agent that increases conductivity of the tissue or enhances softening, stiffening or other tissue changes. Such an injection may be performed using conventional techniques and device, such as a syringe, or alternatively a treatment device may include a built-in injection device.

In another aspect of the disclosure, a device for treating a soft palate in a patient to treat sleep apnea, snoring or both may include a handle, a shaft, a treatment element, and a connector for connecting the handle with a power source. The shaft may include a distal end with a neck, and the treatment element may extend from the neck and may be angled relative to a longitudinal axis of the shaft. The treatment element may include a treatment surface and at least one energy delivery member on the treatment surface. In some embodiments, the energy delivery member comprises two rows of bipolar, radiofrequency electrode pairs protruding from the tissue-contact surface. The electrodes may be triangular in shape, for example. In some embodiments, the treatment surface has a convex shape for creating a concave deformity in the soft palate. In some embodiments, the device may have multiple shafts and multiple treatment elements, where each of the treatment elements is located on one of the multiple shafts.

These and other aspects and embodiments are described further below, in relation to the attached drawing figures.

BRIEF DESCRIPTION OF DRAWINGS

Certain embodiments and modifications thereof will become apparent from the detailed description below, having reference to the figures that follow.

FIGS. 1A-1G are various views of a device for applying energy to the soft palate for treating OSA and/or snoring, according to one embodiment;

DETAILED DESCRIPTION

Figure 1A:
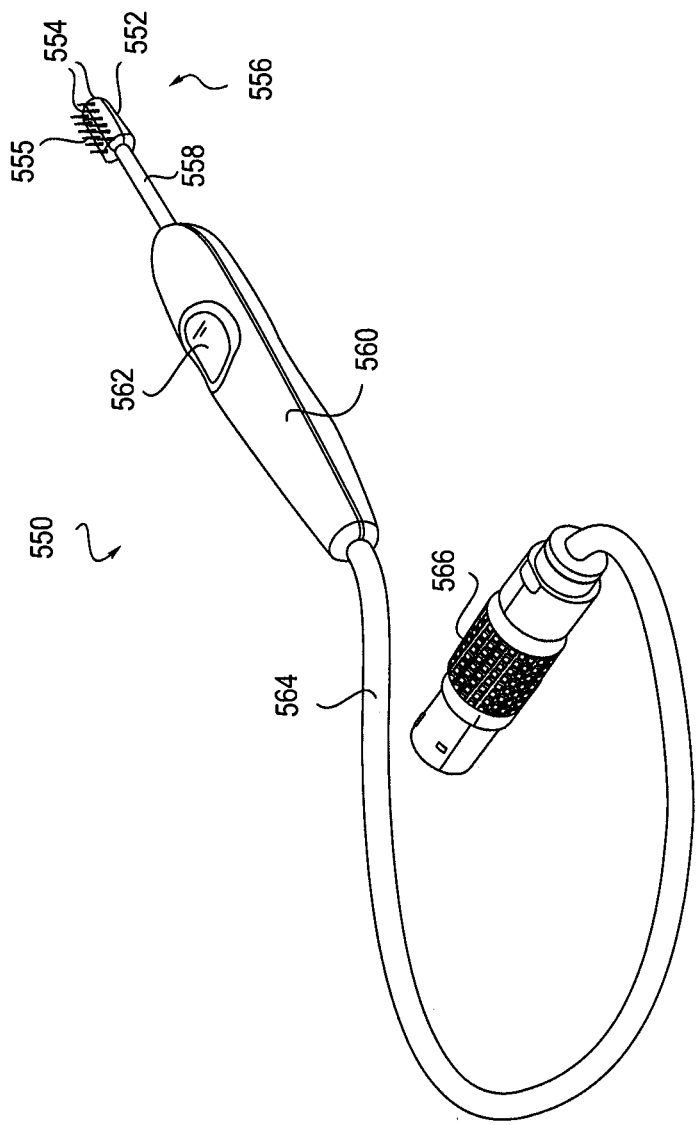

The assignee of the present application has developed a number of devices, systems and methods for delivering energy to tissues in the nasal passages to treat nasal valve insufficiency, post nasal drip and other breathing abnormalities and disorders of the nasal passages. The systems generally include an energy delivery console (or "box") and a hand piece for delivering the therapy to the nasal tissue. The hand piece typically includes a handle, a shaft, and a treatment delivery element at or near the end of the shaft for delivering the energy to the tissues. One general type of embodiment includes one handle, one shaft and one treatment element for advancing through a nostril. Another general type of embodiment includes a clamp-like configuration, with two handles, two shafts and two treatment elements, where tissue is clamped between the two tissue elements, which are either advanced through both nostrils or through one nostril and an outside of the nose. In general, the method of treatment involves applying force to a tissue to be treated with the treatment element, to deform the tissue, and applying energy to the tissue with the treatment element. When the treatment is stopped and the treatment element is removed, the target tissue is reformed or changed in some other way and retains at least some of that change after the treatment is complete. In one embodiment, the treatment element delivers bipolar radiofrequency (RF) energy from multiple electrodes on the treatment element, although many other energy modalities and treatment element configurations are possible.

Patents describing various embodiments of these tissue treatment devices, systems and methods include U.S. Pat. Nos. 8,936,594; 9,237,924; 9,433,463; 9,415,194; 9,452,087 and 9,433,463. All of these patents, referred to herein as "the Incorporated Patents," are hereby incorporated by reference herein in their entireties. Any of the embodiments described in the Incorporated Patents may be used or adapted for use in treating the soft palate and/or other mouth or throat structures to treat OSA and/or snoring. The many embodiments of methods, devices and systems described in the Incorporated Patents will not be repeated in this application, but again, any embodiments described there may be used or adapted for use in performing the methods described herein for treating OSA and/or snoring.

FIGS. 1A-1G illustrate one embodiment of a treatment device 550 described in the Incorporated Patents. Device 550 may include a handle 560, a shaft 558, and a treatment element 552 that is attached to (or simply a distal portion of) at a distal tip 556 of device 550. Treatment element 552 may be provided on an enlarged distal tip 556 of elongate shaft 558, and as in the embodiment illustrated, may have a convex shape configured to press against and create a concavity in the soft palate tissue, such as cartilage and mucosa. Treatment element 552 may include two rows of protruding RF electrodes 554 and a thermocouple 555. In this embodiment, electrodes 554 are shown as needle electrodes, but in alternative embodiments electrodes 554 may be protruding but not piercing or may be non-protruding. Handle 560 may include an input control, such as a power button 562, on its front side that may be used to activate and deactivate treatment element 522. Power button 562 may be positioned in a recess of the handle to allow for finger stability when activating and deactivating the electrode. In other embodiments, the input control is in the form of a switch or dial or foot pedal.

Device 550 may either include a generator or be connected to a remote generator. Device 550 may include a flexible wire or cable 564 that connects to an adaptor 566 that is configured to be plugged into a remote generator (not shown). Adaptor 566 may allow transmission of treatment energy between a remote generator and the device 550. Adaptor 566 may also allow transmission of any sensor signals between device 550 and a generator or control unit. Treatment device 550 may be provided in a system or kit also including the remote generator. The system or kit (with or without the remote generator) may also include a grounding device and/or a cooling device as described above and further below. In some embodiments, the kit includes a positioning element (e.g., a "cottle" device) configured to help a user locate the optimal treatment area.

In some embodiments, shaft 558 has a width or diameter or about 0.235 inches to about 0.25 inches. In some embodiments, the shaft is about 1.5 inches to about 4 inches long. In some embodiments, the shaft and/or handle is made of a polymer such as polycarbonate or PEEK. In other embodiments, the shaft is made of stainless steel or other metals. The metals may be coated with an external and/or internal insulating coating (e.g., polyester, polyolefin, etc.). Handle 560 may be made of the same material as shaft 558, in some embodiments. In some embodiments, the shaft 558 is rigid. This may allow a user of device 550 increased control over the deformation of soft palate tissue. In other embodiments, shaft 558 may be flexible. This flexibility may allow a user adjust an angle of distal tip 556 by bending shaft 558. In some embodiments, this tip-to-shaft angle may be adjustable, for example via a locking hinge or other similar mechanism. In some embodiments, distal tip 556 may be flexible or pre-curved along its length, so that it better conforms to the tissue of the soft palate.

Figure 1B:
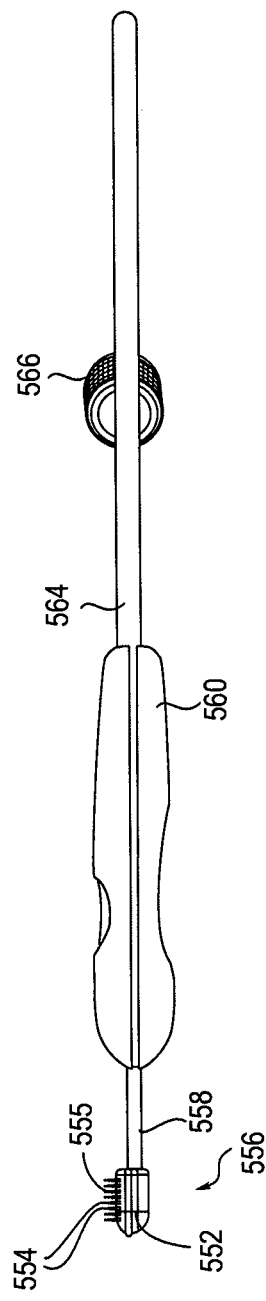
Figure 1C:
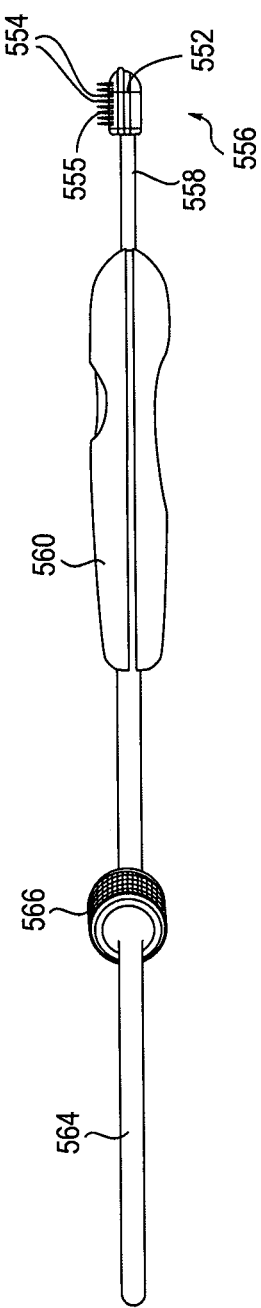
Figure 1D:
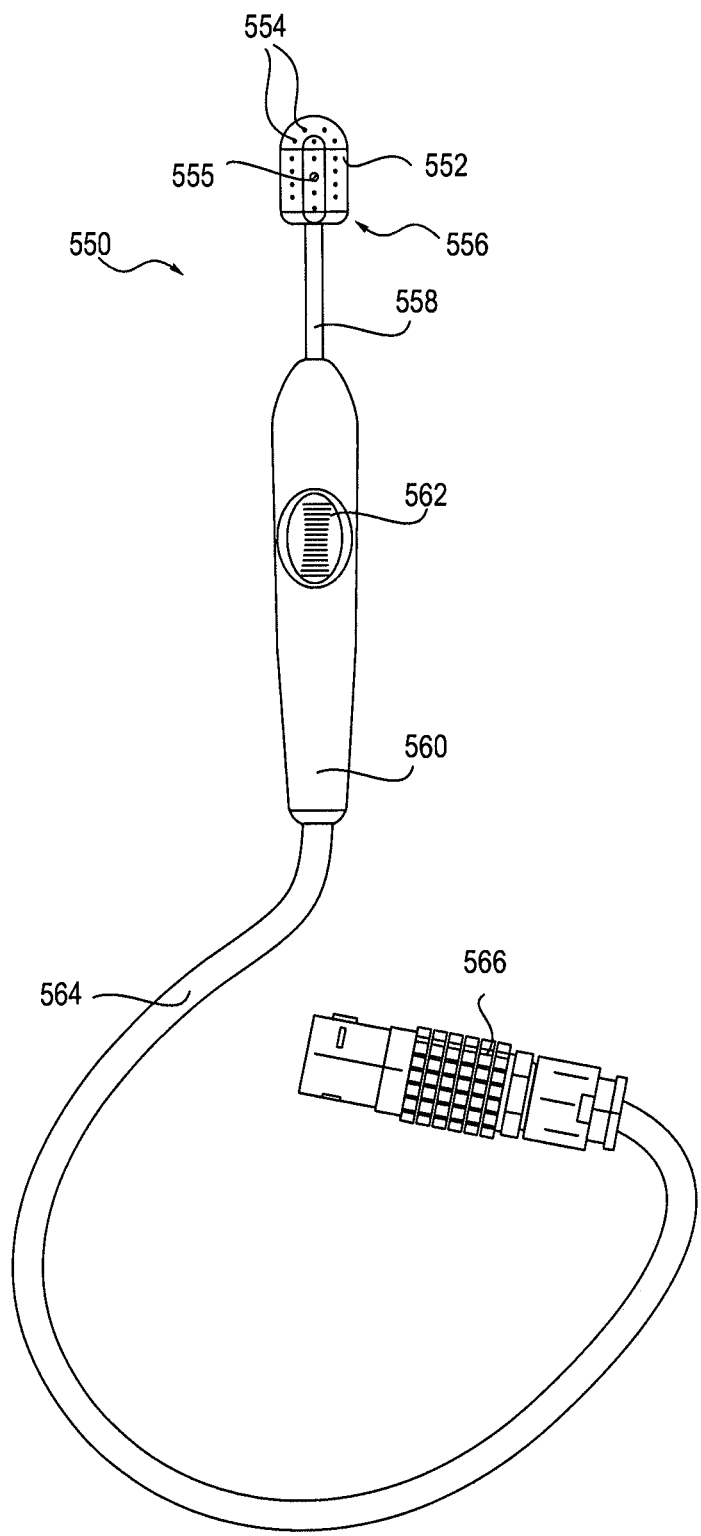
Figure 1E:
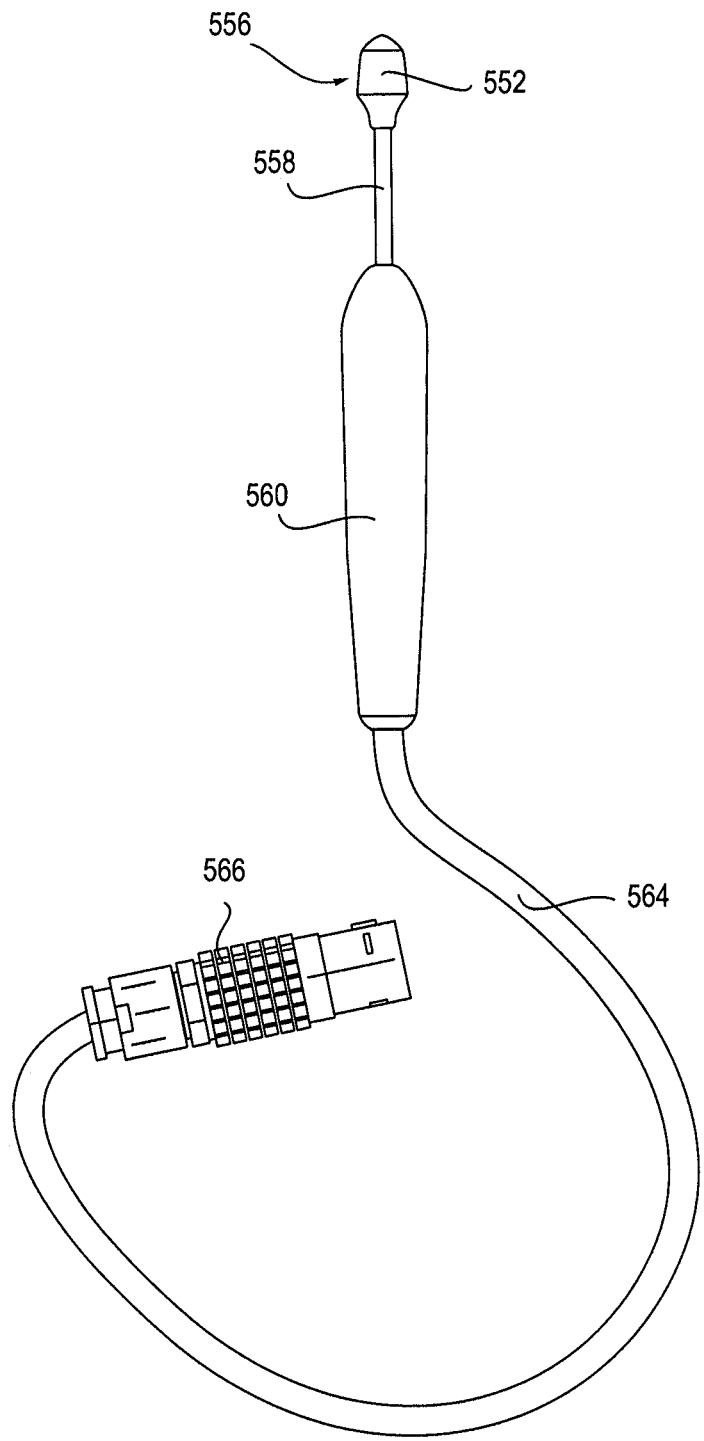

FIGS. 1B and 1C depict side views of device 550. FIGS. 1D and 1E depict front and back views, respectively, of device 550. As shown in FIGS. 1D and 1E, handle 560 generally comprises a rounded elongate shape. Other shapes are also possible. For example device 550 may have a square shaped cross section. In some embodiments, a circumference (or width or cross-sectional area) of handle 560 may increase distally along the length of handle 560.

FIG. 1G depicts a larger view of distal tip 556 of device 550. As shown best in FIG. 1G, treatment element 552 comprises a generally elongate shape. The front of treatment element 552 comprises a shallow curved surface, providing a convex shape configured to deform the soft palate tissue and create a concavity therein. In alternative embodiments, the front of treatment element 552 comprises a concave shape. The shape of the front surface of treatment element 552 may be selected to conform to the soft palate tissue. The back surface of treatment element 552 comprises a shallow curved surface along most of its length. As best seen in FIGS. 1B and 1C, the back surface narrows distally along the length of the element 552, from approximately the distal end of the needle electrodes to the distal tip of the treatment element 552. This shape may maximize visualization of the area to be treated, while, at the same time, providing sufficient rigidity for treatment. Other shapes are also possible. For example, treatment element 552 may have a generally spherical or cylindrical shape. In some embodiments, treatment element 552 comprises an angular shape (e.g., triangular, conical), which may allow for close conformation to the tissue structures.

Treatment element 552 may include a monopolar or bipolar array of RF needles 554. In some embodiments, needles 554 are energized in between select needles to deliver bipolar energy. In other embodiments, the energy is delivered between needles 554 and a remote grounding pad (not shown). In some embodiments, electrode needle pairs 554 are arranged horizontally across treatment element 552. In some embodiments, electrode needle pairs 554 are arranged vertically across treatment element 552, or along the direction of shaft 558 and handle 560. Other configurations are also possible. For example, needle pairs 554 may be arranged diagonally across treatment element 552. Treatment element 552 may be placed either internally, with needle pairs 554 positioned transmucosally, or treatment element 552 may be placed externally with needle pairs 554 positioned transdermally. Distal tip 556 of device 550 may also function as a mold or molding element. In a monopolar embodiment, the energy may be selectively delivered between certain sets of needles, all needles, or even individual needles to optimize the treatment effect.

Treatment element 552 of the device 550 further comprises a pin-shaped structure comprising a thermocouple 555 within an insulating bushing extending through a middle portion of the front surface of the treatment element 552. In some embodiments, different heat sensors (e.g., thermistors) may be used. In some embodiments, thermocouple 555 may be configured to measure a temperature of the surface or subsurface of tissue to be treated or tissue near the tissue to be treated. A pin shape having a sharp point may allow the structure to penetrate the tissue to obtain temperature readings from below the surface. Thermocouple 555 can also be configured to measure a temperature of the treatment element 552. The temperature measurements taken by thermocouple 555 can be routed as feedback signals to a control unit, and the control unit can use the temperature measurements to adjust the intensity of energy being delivered through electrodes 554. In some embodiments, thermocouple 555 or other sensing devices may be used to measure multiple tissue and device parameters. For example, multiple thermocouples 555 or thermistors may be used to measure a temperature at different locations along the treatment element. In some embodiments, one of the sensors may be configured to penetrate deeper into the tissue to take a measurement of a more interior section of tissue. For example, device 550 may have multiple sensors configured to measure a temperature at the mucosa, the cartilage, and/or treatment element 552. As described above, in some embodiments, the sensors described herein are configured to take a measurement of a different parameter. For example, tissue impedance can be measured. These measurements can be used to adjust the intensity and/or duration of energy being delivered through the treatment element. This type of feedback may be useful from both an efficacy and a safety perspective.

In some embodiments, treatment element 552 has a width or diameter of about 0.25 inches to about 0.45 inches. In some embodiments, treatment element 552 is about 0.4 inches to about 0.5 inches long. Treatment element 552 can, in some embodiments, comprise a ceramic material (e.g., zirconium, alumina, silicon glass). Such ceramics may advantageously possess high dielectric strength and high temperature resistance. In some embodiments, treatment element 522 may include polyimides or polyamides, which may advantageously possess good dielectric strength and elasticity and be easy to manufacture. In some embodiments, treatment element 552 may include thermoplastic polymers. Thermoplastic polymers may advantageously provide good dielectric strength and high elasticity. In some embodiments, treatment element 552 may include thermoset polymers, which may advantageously provide good dielectric strength and good elasticity. In some embodiments, treatment element 552 may include glass or ceramic infused polymers. Such polymers may advantageously provide good strength, good elasticity, and good dielectric strength.

In some embodiments, electrodes 554 have a width or diameter of about 0.15 inches to about 0.25 inches. In some embodiments, electrodes 554 are about 0.2 inches to about 0.5 inches long. In some embodiments, electrodes 554 may be made of steel (e.g., stainless, carbon, alloy). Steel may advantageously provide high strength while being low in cost and minimally reactive. In some embodiments, electrodes 554 or other energy delivery elements described herein comprise materials such as platinum, gold, or silver. Such materials may advantageously provide high conductivity while being minimally reactive. In some embodiments, electrodes 554 or other energy delivery elements described herein may include titanium, which may advantageously possess a high strength to weight ratio and be highly biocompatible. In some embodiments, electrodes 554 or other energy delivery elements described herein may include nickel titanium alloys. These alloys may advantageously provide high elasticity and be biocompatible. Other similar materials are also possible.

Energy applied to the tissue to be treated using any combination of the embodiments described in this application may be controlled by a variety of methods. In some embodiments, temperature or a combination of temperature and time may be used to control the amount of energy applied to the tissue. Tissue is particularly sensitive to temperature, so providing just enough energy to reach the target tissue may provide a specific tissue effect, while minimizing damage resulting from energy causing excessive temperature readings. For example, a maximum temperature may be used to control the energy. In some embodiments, time at a specified maximum temperature may be used to control the energy. In some embodiments, thermocouples, such as those described above, are provided to monitor the temperature at the electrode and provide feedback to a control unit. In some embodiments, tissue impedance may be used to control the energy. Impedance of tissue changes as it is affected by energy delivery. By determining the impedance reached when a tissue effect has been achieved, a maximum tissue impedance can be used to control energy applied.

In the embodiments described herein, energy may be produced and controlled via a generator that is either integrated into the electrode hand piece or as part of a separate assembly that delivers energy or control signals to the hand piece via a cable or other connection. In some embodiments, the generator is an RF energy source configured to communicate RF energy to the treatment element. For example, the generator may comprise a 460 KHz sinusoid wave generator. In some embodiments, the generator is configured to run between about 1 and 100 watts. In some embodiments, the generator is configured to run between about 5 and about 75 watts. In some embodiments, the generator is configured to run between about 10 and 50 watts.

In some embodiments, the energy delivery element comprises a monopolar electrode. Monopolar electrodes are used in conjunction with a grounding pad. The grounding pad may be a rectangular, flat, metal pad. Other shapes are also possible. The grounding pad may comprise wires configured to electrically connect the grounding pad to an energy source (e.g., an RF energy source).

In some embodiments, the energy delivery element such as the electrodes described above can be flat. Other shapes are also possible. For example, the energy delivery element can be curved or comprise a complex shape. For example, a curved shape may be used to place pressure or deform the tissue to be treated. The energy delivery element may comprise needles or microneedles. The needles or microneedles may be partially or fully insulated. Such needles or microneedles may be configured to deliver energy or heat to specific tissues while avoiding tissues that should not receive energy delivery.

In some embodiments, the non-electrode portion of treatment element 552 may include an insulating material, such as a ceramic material (e.g., zirconium, alumina, silicon glass). In some embodiments, treatment elements 552 may include an insulating material interposed between multiple electrodes 554 or electrode sections. These insulating sections may provide an inert portion of the treatment element that does not delivery energy to the tissue. Such ceramics may advantageously possess high dielectric strength and high temperature resistance. In some embodiments, the insulators described herein comprise polyimides or polyamides which may advantageously possess good dielectric strength and elasticity and be easy to manufacture. In some embodiments, the insulators described herein comprise thermoplastic polymers. Thermoplastic polymers may advantageously provide good dielectric strength and high elasticity. In some embodiments, the insulators described herein comprise thermoset polymers, which may advantageously provide good dielectric strength and good elasticity. In some embodiments, the insulators described herein comprise glass or ceramic infused polymers. Such polymers may advantageously provide good strength, good elasticity, and good dielectric strength.

In some embodiments, handle 560 and/or shaft 558 may include the same materials as those described with respect to the insulators. In some embodiments, handle 560 and/or shaft 558 may include a metal, such as stainless steel. In other embodiments, handle 560 and/or shaft 558 may include a polymer, such as polycarbonate. Other metals and polymers are also contemplated.

In some embodiments, device 550 may be used in conjunction with a positioning element that can be used to aid in positioning of the device. The positioning element may be integrated into the device itself or can be separate. The positioning element may be used to determine the optimal placement of the device to achieve maximal increase in efficacy. In some embodiments, a positioning element is configured to be inserted and manipulated within the mouth until the patient reports a desired improvement in breathing. Device 550 may then be used to treat, while the positioning element is holding the mouth in the desired configuration. In some embodiments, molds described herein may be used for the same purpose.

In some embodiments, a positioning element may include a shaft, including measurement marks indicating depth. For example, a physician may insert this element into the mouth to manipulate the tissue to find the depth of treatment at which the soft palate is contacted. The positioning element may also comprise marks indicating angle of insertion. The physician may then use the measurement marks to guide insertion of the treatment element to the same spot.

Embodiments of devices configured to heat specific tissue while maintaining lower temperatures in other adjacent tissue are provided. These devices may be incorporated into any of the treatment apparatuses and methods described herein. The soft palate is an example of a tissue complex that includes adjacent tissues that may benefit from being maintained at different temperatures. Other examples include the skin, which comprises the epidermis, dermis, and subcutaneous fat, the tonsils, which comprise mucosa, glandular tissue, and vessels. Treatment of other tissue complexes is also possible. For example, in some embodiments, the internal structures of the soft palate may be heated, while maintaining a lower temperature in the mucosal lining of the mouth and/or skin. In other embodiments, the mucosa may be heated, while maintaining lower temperatures in the skin. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cartilage, while excluding another tissue, such as mucosa, without surgical dissection.

Figure 2:
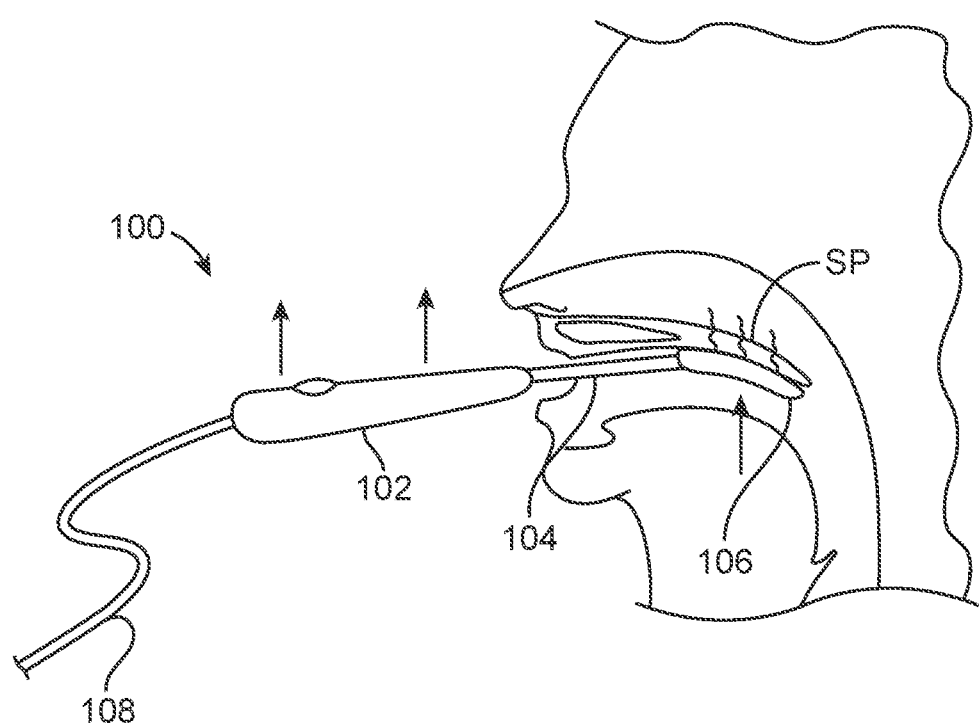
FIG. 2 is a side/cross-sectional view of a patient's head and a side view of a device being applied to the soft palate to treat OSA and/or snoring, according to one embodiment.

Referring now to FIG. 2, a method for treating soft palate SP tissue is illustrated. In the embodiment shown, a soft palate tissue treatment device 100 includes a handle 102, a shaft 104, a treatment element 106 and a cord 108. In use, treatment element 106 is advanced into the patient's mouth, and an upper surface (or "treatment surface") of treatment element 106 is contacted with the mucosa of the soft palate. In some embodiment, the physician, physician's assistant or other user of device 100 may apply upwardly directed force (solid-tipped arrows) to treatment element 106, by pulling up on handle 102, thus deforming a portion of the soft palate SP. While holding the soft palate in the deformed configuration, energy (wavy lines) may be delivered to the tissue via multiple RF electrodes or other energy delivery devices on the upper, treatment surface of treatment element 106. Force and energy may be applied in any suitable amount and for any suitable length of time, according to treatment goals, patient anatomy, treatment protocols and/or the like. In some embodiments, device 100 may be removed from the patient's mouth after one area of the soft palate is treated. Alternatively, after a first treatment, treatment element 106 may be moved to a second area of treatment, and another treatment may be delivered. This may be repeated as many times as desired, to cover a desired treatment area.

As mentioned above, the treatment may be used to change the shape, strength, stiffness or any other property of any soft palate tissue, such as but not limited to mucosa, cartilage and collagen. In embodiments where the shape of the soft palate is changed during the treatment, at least some of this change in shape will be retained after the treatment. In addition to treating the soft palate, some treatment method embodiments may also include treating other nearby tissues of the mouth, throat, tongue, etc. Also, the upper, treatment surface portion of treatment element 106 may include any suitable energy delivery device and may have any suitable shape for addressing the soft palate. For example, treatment element 106 may deliver energy in the form of bipolar RF, monopolar RF, ultrasound, cryotherapy (energy removal), heat, chemical, microwave or any other suitable type of energy, and it may include any number of energy delivery members. The shape of the treatment surface may be convex, concave or flat and may have any shape, such as ovoid, rectangular, triangular, asymmetric, etc.

Figure 3:
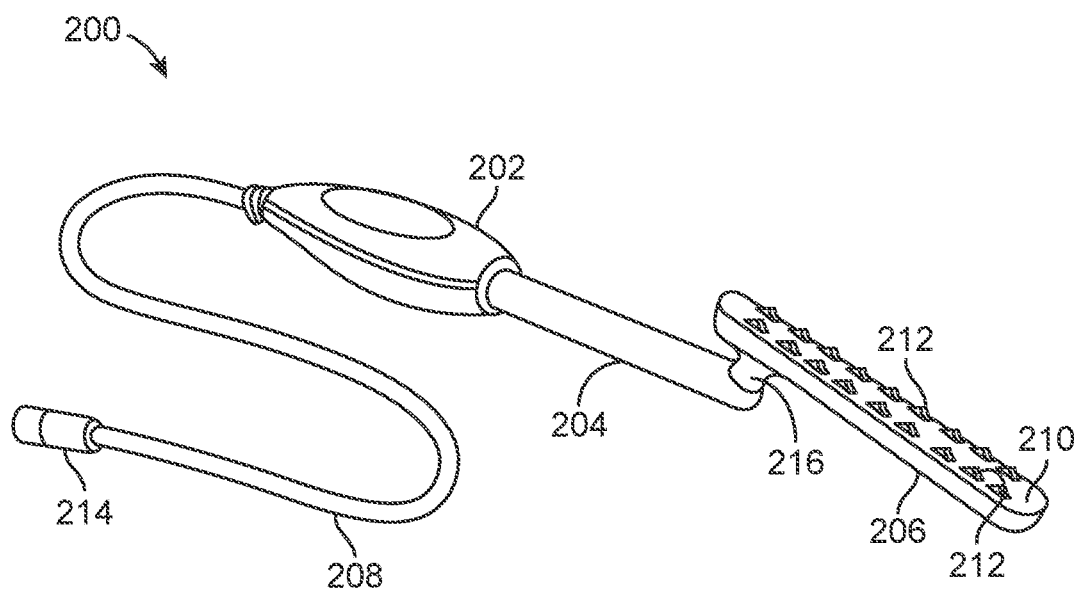
FIG. 3 is a perspective view of a device for applying energy to the soft palate for treating OSA and/or snoring, according to an alternative embodiment.

Referring to FIG. 3, an alternative embodiment of a soft palate treatment device 200 may include a handle 202, a shaft 204, an elongate treatment element 206, a power/energy delivery cable 208, and an adapter 214 for connected with a power/energy source. In this embodiment, shaft 204 may include a neck 216, so that treatment element 206 is angled slightly, relative to the longitudinal axis of shaft 204. Alternatively, treatment element 206 may be parallel with shaft 204, coaxial with shaft 204, or have any other position relative to shaft 204. Treatment element 206 may include an upper treatment surface 210 and multiple RF electrodes 212 arrayed along surface 210 in two parallel rows. In this embodiment, surface 210 is relatively long and straight, with curved ends, and electrodes 212 are shaped as triangular protrusions from surface 210, are aligned in two rows, and are bipolar RF electrodes 212. As mentioned above, in alternative embodiments, treatment element 206, treatment surface 210 and electrodes 212 may have any other suitable shapes, numbers and configurations, and in some embodiments, alternative energy delivery members may be used. Handle 202 may either be rigidly or flexibly attached to shaft 204, thus potentially allowing for relative movement between these two components in some embodiments. In some embodiments, electrodes 212 may be moveable, relative to treatment element 206, for example in and out of surface 210 or along surface 210 laterally.

As illustrated, in this embodiment, treatment surface 210 is relative long and flat. This shape may be ideal for treating soft palate (and possibly other tissue in the mouth or throat) to treat OSA and/or snoring. On the other hand, treatment surface 210 may have a convex or other shape in alternative embodiments, to help deform soft palate tissue into a desired configuration. Whatever the shape of surface 210, electrodes 212 are used to apply RF energy to the target tissue, to cause heating and eventual shrinking, stiffening and/or reshaping of the soft palate. The resulting treatment effect may include volume reduction, tissue stiffening (higher modulus) and/or stiffening by way of more optimal structure (e.g., arched tissue with a higher second moment of inertia, better bending stiffness, etc.). Radiofrequency energy may be controlled via temperature feedback, such as a thermocouple and RF power controller, and/or may be controlled to impart a specific total energy. Device 200 may also be used with minimal built-in control and applied by the physician under visualization until the intended effect on the target tissue has been achieved. In alternative embodiments, alternate energy sources may include cryogenic surface cooling, combinations of cooling and heating technologies, cauterizing agents, ultrasound or the like.

Figure 4:
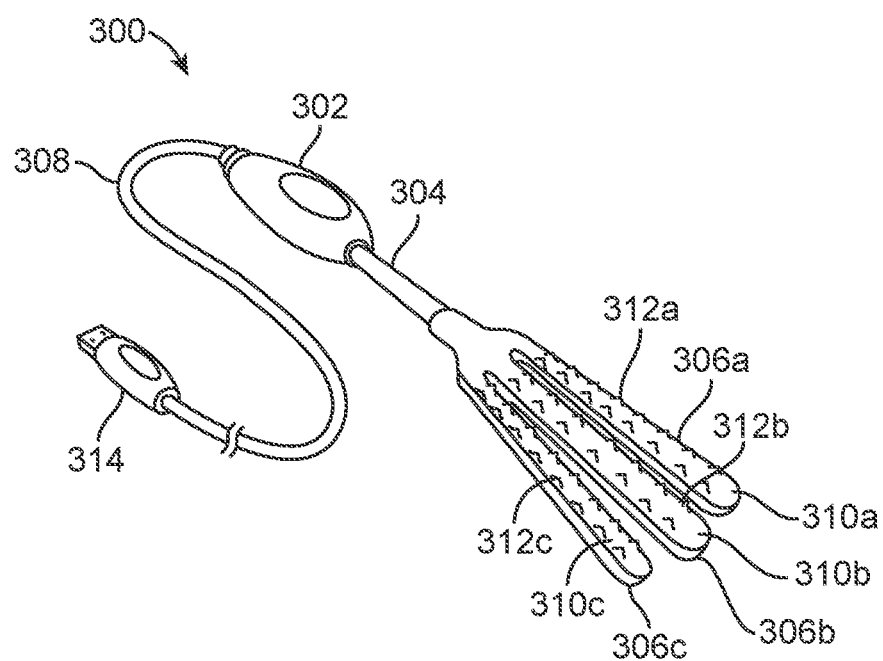
FIG. 4 is a perspective view of a device for applying energy to the soft palate for treating OSA and/or snoring, according to another alternative embodiment.

With reference now to FIG. 4, another alternative embodiment of a soft palate treatment device 300 may include a handle 302, a shaft 304, three treatment elements 306a-c, a power/energy delivery cable 308, and an adapter 314 for connected with a power/energy source. In this embodiment, shaft 304 is on the same vertical plane as treatment elements 306a-c. Treatment element 306a-c include upper treatment surfaces 310a-c and multiple RF electrodes 312a-c arrayed along surfaces 310a-c in two parallel rows. This configuration and number of treatment elements 306a-c may be ideal for addressing a larger area of the soft palate in one treatment.

Again, any of the embodiments described in the Incorporated Patents may be used to treat the soft palate for addressing OSA and/or snoring, and any features described in the Incorporated Patents may be incorporated into the designs described herein.

Figure 5:
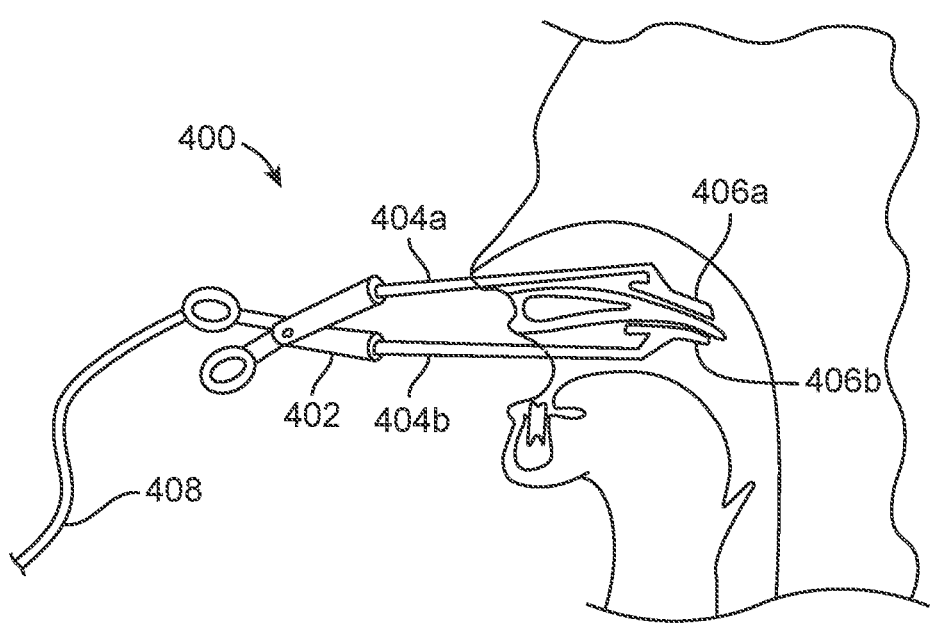
FIG. 5 is a side/cross-sectional view of a patient's head and a side view of a device being applied to the soft palate to treat OSA and/or snoring, according to another alternative embodiment.

Referring now to FIG. 5, in another alternative embodiment, a soft palate treatment device 400 may include a handle 402 that acts like a clamp or scissors handle, two shafts 404a-b extending from handle 402, two tissue treatment elements 406a-b (one at the end of each shaft 404a-b), and a power/energy cable 408. This embodiment of device 400 is similar to the clamp-type devices described in the Incorporated Patents, although it may be sized and/or shaped differently, to address the soft palate. In this embodiment, one shaft 404a is configured to extend through a nostril, so that its corresponding treatment element 406a contacts an upper surface of the soft palate, and the other shaft 404b is configured to extend through the mouth, so that its corresponding treatment element 406b contacts a lower surface of the soft palate. Treatment elements 406a-b can then be used to clamp the soft palate tissue between them and, in some embodiments, to alter the shape of the tissue. Energy may then be delivered from both treatment elements 406a-b or alternatively from one treatment element 406a or 406b, across the tissue to the other element. In some embodiments, shafts 404a-b and treatment elements 406a-b may be exactly or almost exactly the same, in terms of diameter, length and shape. Alternatively, one shaft 404a-b and/or one treatment element 406a-b may be smaller, for fitting through a nostril, and the other may be larger, for fitting through the mouth.

Again, any of the features described in the Incorporated Patents may be incorporated into device 400, according to various embodiments. Although no incisions have been described above, in some embodiments, the treatment method may involve forming a small incision in the mucosa of the soft palate and advancing the treatment element through the incision to contact and treat tissue underlying the mucosa. Such embodiments are described more fully in some of the Incorporated Patents.

Although various embodiments are described herein, the present invention extends beyond the specifically disclosed embodiments to other alternative embodiments and/or uses of the invention and modifications and equivalents thereof. Thus, the scope of the present invention should not be limited by the disclosed embodiments, but should be determined only by a fair reading of the claims that follow.

What is claimed is:

1. A method of treating a soft palate in a patient, without forming an incision or piercing a mucosal surface of the soft palate, to treat sleep apnea, snoring or both, the method comprising:

advancing a treatment element of a treatment device through the patient's mouth;

contacting a tissue-contact surface of the treatment element with the mucosal surface lining the soft palate, without piercing the mucosal surface;

delivering radiofrequency energy from a radiofrequency sinusoid wave generator coupled with a handle of the treatment device to multiple bipolar radiofrequency electrodes on the tissue-contact surface of the treatment element;

delivering the radiofrequency energy from a first row of the multiple bipolar radiofrequency electrodes through the mucosal surface, through an internal tissue of the soft palate, and to a second row of the multiple bipolar radiofrequency electrodes, to heat and change a property of the internal tissue without damaging the mucosal surface;

measuring a temperature of the mucosal surface with at least one sensor on the tissue-contact surface of the treatment element;

providing the temperature to a control unit coupled with the treatment device; and adjusting, with the control unit, an amount of the radiofrequency energy delivered by the multiple bipolar radiofrequency electrodes, based on the temperature.

2. A method as in claim 1, wherein the multiple bipolar radiofrequency electrodes comprise protruding, non-penetrating electrodes, and wherein delivering the radiofrequency energy at least one of reshapes, remodels, stiffens, shrinks an strengthens the internal tissue of the soft palate.

3. A method as in claim 2, wherein the treatment device further comprises:
a shaft extending from the handle and defining a longitudinal axis; and
a neck disposed between the shaft and the treatment element, wherein the treatment element is attached to the neck so as to position the treatment element at an angle relative to the longitudinal axis of the shaft.

4. A method as in claim 1, further comprising applying force against the soft palate with the tissue-contact surface while delivering the energy, to at least temporarily deform the internal tissue of the soft palate, wherein the internal tissue at least partially retains a deformed shape after the treatment device is removed from the patient's mouth.

5. A method as in claim 1, wherein the internal tissue of the soft palate is selected from the group consisting of submucosal tissue, cartilage and collagen.

6. A method as in claim 1, wherein the radiofrequency sinusoid wave generator comprises a 460 kHz radiofrequency sinusoid wave generator.

7. A method as in claim 1, wherein delivering the energy to the internal tissue of the soft palate comprises heating the internal tissue, the method further comprising maintaining the temperature of the mucosal surface at a lower temperature than a heated temperature of the internal tissue.

8. A method as in claim 1, wherein the at least one sensor comprises at least one thermocouple positioned between at least two of the multiple bipolar radiofrequency electrodes.

* * * * *